(12) United States Patent
Vogel

(10) Patent No.: US 12,397,137 B2
(45) Date of Patent: Aug. 26, 2025

(54) NESTED BALLOON ASSEMBLY

(71) Applicant: MEDTRONIC VASCULAR, INC., Santa Rosa, CA (US)

(72) Inventor: Jeffrey Vogel, Brooklyn Park, MN (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 481 days.

(21) Appl. No.: 17/206,203

(22) Filed: Mar. 19, 2021

(65) Prior Publication Data
US 2021/0330945 A1    Oct. 28, 2021

Related U.S. Application Data

(60) Provisional application No. 63/015,305, filed on Apr. 24, 2020.

(51) Int. Cl.
*A61M 25/10* (2013.01)

(52) U.S. Cl.
CPC .... *A61M 25/1011* (2013.01); *A61M 25/1029* (2013.01)

(58) Field of Classification Search
CPC .......... A61M 25/1029; A61M 25/1011; A61M 2025/1013; A61M 2025/1059; A61M 2025/1075
See application file for complete search history.

(56) References Cited

U.S. PATENT DOCUMENTS

| | | | |
|---|---|---|---|
| 5,342,305 A * | 8/1994 | Shonk | A61M 25/104 604/101.02 |
| 5,358,487 A | 10/1994 | Miller | |
| 7,052,510 B1 | 5/2006 | Richter | |
| 2002/0091435 A1 | 7/2002 | Campbell | |
| 2014/0142505 A1* | 5/2014 | Lin | A61M 25/1029 604/103.06 |
| 2018/0036518 A1 | 2/2018 | Yang et al. | |

FOREIGN PATENT DOCUMENTS

WO    WO2001095833 A2    12/2001

OTHER PUBLICATIONS

Extended European Search Report from EP 21168805.6-1132, mailed Sep. 29, 2021, 12 pages.

\* cited by examiner

*Primary Examiner* — Diane D Yabut
(74) *Attorney, Agent, or Firm* — Stinson LLP

(57) ABSTRACT

A medical balloon assembly including an inner balloon nested within an outer balloon. The inner balloon has a first target burst pressure at which the inner balloon bursts and the outer balloon has a second target burst pressure at which the outer balloon bursts. A differential between the first and second target burst pressures is sufficient to allow the outer balloon to remain intact upon inflation of the inner and outer balloons causing the inner balloon to burst.

20 Claims, 2 Drawing Sheets

NESTED BALLOON ASSEMBLY

CROSS-REFERENCE TO RELATED APPLICATIONS

This application claims priority to U.S. Provisional Patent Application No. 63/015,305, entitled NESTED BALLOON ASSEMBLY and filed Apr. 24, 2020, which is hereby incorporated by reference in its entirety.

FIELD

This disclosure is related generally to a nested balloon assembly.

BACKGROUND

Balloons mounted on the distal ends of catheters or other medical devices are widely used in medical treatment. For example, a medical balloon may be used to widen a vessel into which the catheter is inserted, open a blocked vessel and/or deliver a medical device (e.g., a stent) to a treatment location inside a body, among other uses. In use, the balloon is delivered to a treatment location by inserting the balloon in an uninflated configuration through a body lumen (e.g., a blood vessel). Balloons can be inserted through a body lumen by tracking the uninflated balloon through an introducer sheath and/or along a guidewire. Once the uninflated balloon has reached the treatment location, fluid is delivered into the balloon, thereby expanding the outer circumference of the balloon (i.e., the balloon is inflated). After treatment, the balloon is deflated and withdrawn from the patient's body. In some cases, the balloon may later be re-introduced into the same or another body lumen of the patient.

Inflation of the balloon exerts pressure on the inside of the balloon, creating stress in the balloon wall. In particular, the balloon wall experiences circumferential stress as a result of the radial outward pressure. The balloon will also experience axial stress as a result of the axial outward pressure. The stresses in the wall of the balloon can cause the balloon to burst (e.g., axial and/or radial burst) which is undesirable during medical treatment.

SUMMARY

In one aspect, a medical balloon assembly generally comprises an inner balloon nested within an outer balloon. The inner balloon has a first target burst pressure at which the inner balloon bursts and the outer balloon has a second target burst pressure at which the outer balloon bursts. A differential between the first and second target burst pressures is sufficient to allow the outer balloon to remain intact upon inflation of the inner and outer balloons causing the inner balloon to burst.

In another aspect, a method of making a medical balloon assembly generally comprises forming a first balloon having a first target burst pressure at which the first balloon bursts. Forming a second balloon having a second target burst pressure at which the second balloon bursts. Nesting the first balloon in the second balloon. A differential between the first and second target burst pressures is sufficient to allow the second balloon to remain intact upon inflation of the first and second balloons causing the first balloon to burst.

In yet another aspect, a medical balloon assembly generally comprises an inner balloon nested within an outer balloon. An interior of the medical balloon assembly is configured to receive air to inflate the inner and outer balloons. The inner and outer balloons are configured such that inflation of the medical balloon assembly to a pressure within the interior that will cause the inner balloon to burst will leave the outer balloon intact.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DISCLOSURE

Figure 1:
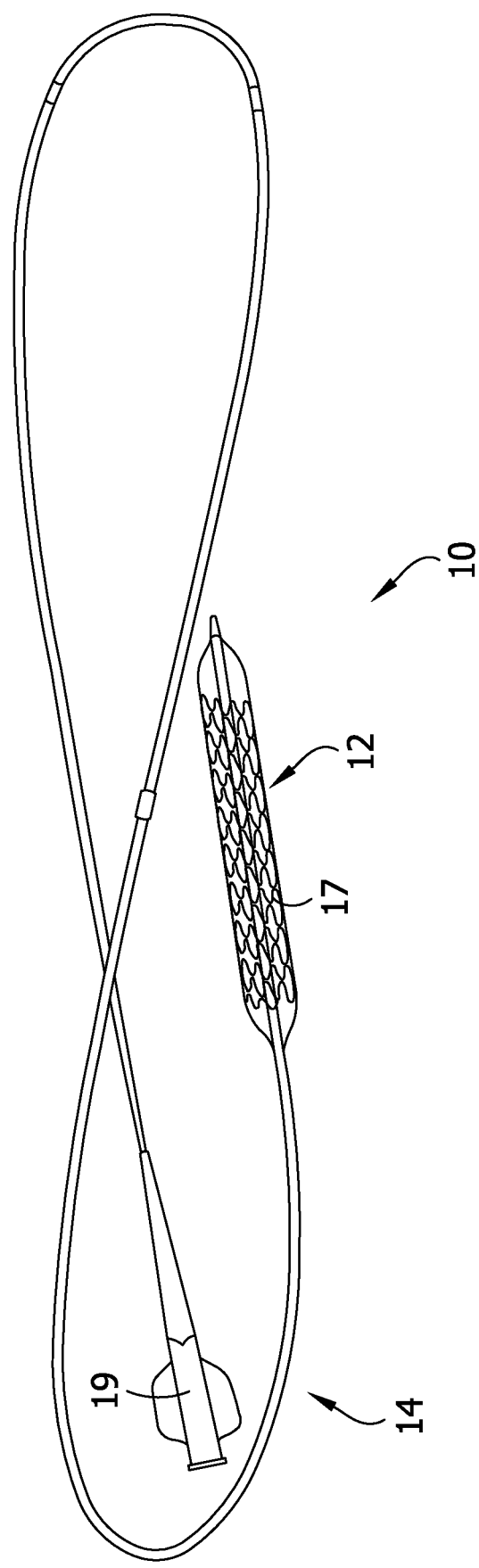
FIG. 1 is a perspective of a balloon catheter.
Figure 2:
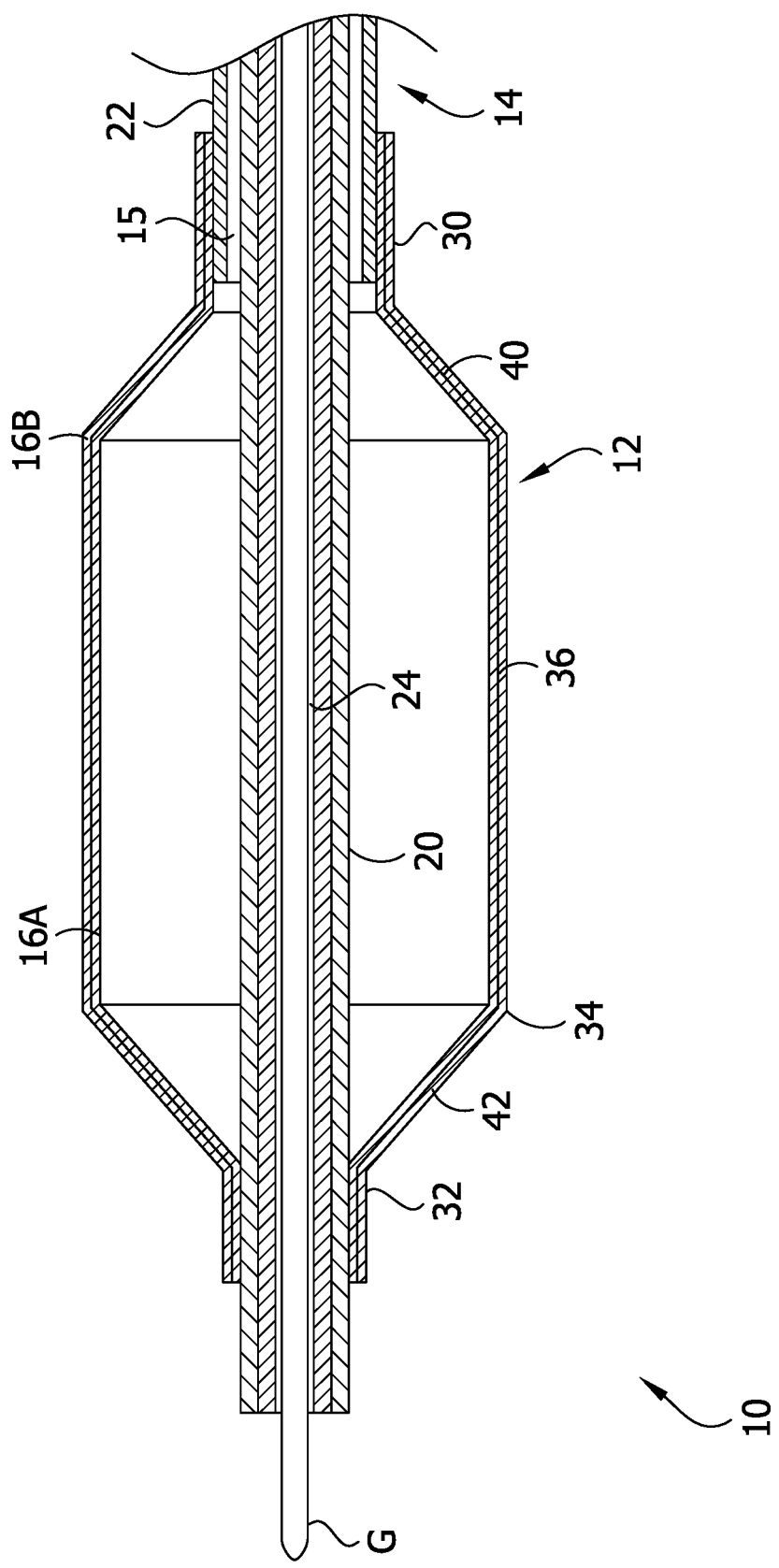
FIG. 2 is a fragmentary longitudinal cross-section of a distal end portion of the balloon catheter of FIG. 1 with a stent thereof removed.

Referring to FIGS. 1 and 2, one embodiment of a balloon catheter is generally indicated at reference number 10. In general, the balloon catheter 10 comprises a medical balloon assembly, generally indicated at 12, and an inflation conduit, generally indicated at 14. The inflation conduit 14 defines an inflation lumen 15 and is fluidly coupled to the balloon assembly 12 to deliver inflation fluid through the inflation lumen to the interior of the balloon assembly. The balloon assembly 12 comprises a plurality of nested balloons including, at least, an inner balloon 16A and an outer balloon 16B. The balloon assembly 12 may include an additional number of balloons without departing from the scope of the disclosure. Additionally, each balloon may comprise one or more layers each having the same or different properties and constructions. The balloons 16 may be formed by any suitable manner such as from parisons or extrusion. As will be explained in greater detail below, the balloon assembly 12 is configured such that relative burst pressures of the inner balloon 16A and outer balloon 16B are selected to optimize an effective or overall burst pressure of the entire balloon assembly to improve the safety profile of the balloon catheter 10. It will be understood that an average burst pressure is the average pressure at which a selection of 10 balloons of the same construction will burst. Thus, a target burst pressure may be associated with a given balloon that is based on the average burst pressure of the selection of balloons of the same construction.

Throughout this disclosure, a "medical balloon assembly" is used to mean a medical device that comprises two or more nested balloons, each constructed according to one or more teachings set forth in the present disclosure. The medical balloon assembly may comprise additional components and/or may be part of a larger assembly. In the illustrated embodiment, the balloon catheter 10 comprises a fully assembled balloon catheter that includes the medical balloon assembly 12, among other components. For example, the balloon catheter 10 may also comprise a stent 17 (FIG. 1) received around the deflated balloon assembly 12. It will be understood that a medical balloon assembly can comprise a subassembly of the balloon catheter. For example, in one or more embodiments, a balloon catheter 10 comprises the medical balloon assembly 12 in a subassembly separate from the inflation conduit 14.

The illustrated inflation conduit 14 is part of an elongate catheter body of the illustrated balloon catheter. The inflation conduit 14 has a proximal end portion connected to an inflation fitting 19, a distal end portion secured to the balloon assembly 12, and a length extending along an axis of the inflation conduit from the proximal end portion to the distal end portion. The inflation fitting 19 is configured to fluidly couple the inflation conduit 15 to a source of inflation fluid (not shown). In one or more embodiments, the inflation lumen 15 extends from the proximal end portion to the distal end portion to provide fluid communication between the source of inflation fluid and the interior of the balloon assembly 12. As shown in FIG. 2, the illustrated inflation conduit 14 comprises an inner inflation tube, generally indicated at reference numeral 20, and an outer inflation tube 22. The inflation lumen 15 is located radially between the inner inflation tube 20 and the outer inflation tube 22. In other embodiments, the inflation conduit can have other configurations (e.g., the inflation conduit can comprise a single tube). In the illustrated embodiment, the inner inflation tube 20 functions as a guidewire tube defining a guidewire lumen 24. The guidewire lumen 24 is configured to slidably receive a guidewire G therein such that the balloon catheter 10 can be advanced along a body lumen by sliding along a preplaced guidewire.

In the illustrated embodiment, each balloon 16A, 16B of the balloon assembly 12 comprises a single piece of monolithic material. For example, in one or more embodiments, the balloons 16A, 16B are formed from a bondable material, such as one of a PEBA and a nylon (e.g., one of PEBAX® elastomer and nylon 12). The balloons can also have other configurations. For example, in one or more embodiments, one or more of the balloons can comprise a multi-layer balloon (e.g., co-extruded, multilayer balloon) or have other arrangements of sections of discrete materials. In certain embodiments, when the balloons are formed from multiple materials, portions (e.g., layers) of the balloon that contact the inflation conduit are formed from bondable materials such that the components of the medical balloon assembly can be secured by direct bonds.

The balloon assembly 12 comprises a proximal neck 30 defining the proximal end of the balloon assembly, a distal neck 32 defining the distal end of the balloon assembly, a length extending along an axis of the balloon assembly from the proximal end to the distal end thereof, and an inflatable portion 34 extending along the length of the balloon assembly between the proximal and distal necks. The inflatable portion 34 of the balloon assembly 12 comprises a body 36, a proximal cone 40 extending between the proximal neck 30 and the body, and a distal cone 42 extending between the distal neck 32 and the body. When inflation fluid is delivered to the interior of the balloon assembly 12 through the inflation conduit 14, the inflatable portion 34 is configured to radially expand from an uninflated configuration (not shown) to an inflated configuration (FIG. 2). In one or more embodiments, in the uninflated configuration of the balloon assembly 12, the inflatable portion 34 comprises folds (e.g., wings) that are configured to wrap circumferentially around the balloon. The balloon can also have other arrangements in the uninflated configuration in certain embodiments. In one or more embodiments, the balloon assembly 12 can be one of non-compliant, semi-compliant, and compliant in the inflated configuration. In the illustrated embodiment, the inflatable portion 34 of the balloon assembly 12 has a generally cylindrical shape having conically tapered end segments in the inflated configuration. In one or more embodiments, the balloon assembly has other shapes in the inflated configuration.

During use, inflation of a nested balloon assembly may cause one of more of the balloons to burst. For instance, at a certain pressure or within a certain pressure range, an inner balloon may burst while an outer balloon remains intact. Conversely, at a certain pressure or within a certain pressure range, an outer balloon may burst while the inner balloon remains intact. Also, within a certain pressure range or above a certain pressure, both the inner and outer balloons may burst. While a balloon burst within a balloon assembly is not ideal, if a burst does occur, it is preferred that the inner balloon burst while keeping the outer balloon intact. It has been found that particularly selecting the individual target burst pressures of the balloons 16A, 16B, and more specifically the relative target burst pressures of the balloons, can increase the effective or overall burst pressure of the balloon assembly 12. Additionally, controlling the relative target burst pressures of the balloons 16A, 16B can configure the balloon assembly 12 such that an inflation level that causes the inner balloon to burst will not also cause the outer balloon to burst.

Generally, in conventional nested balloon assemblies, after one of the balloons bursts, the other balloon(s) will burst as well if the individual burst pressures of the balloons are within a certain threshold. Thus, if the individual burst pressures of the balloons are close enough together, the burst of one balloon will result in the burst of the other balloon. However, in the present disclosure, the relative target burst pressures of the balloons 16A, 16B are maintained above a predetermined threshold to prevent the occurrence where the burst of one balloon results in the burst of the other balloon. For instance, the inner balloon 16A is constructed to have a target burst pressure that is lower than a target burst pressure of the outer balloon 16B by a predetermined amount. In one embodiment, a target burst pressure differential above 1.2 atm provides a sufficient pressure differential so that when the weaker balloon (i.e., lower burst pressure) bursts the stronger balloon (i.e., higher burst pressure) will remain intact. In one embodiment, the pressure differential may be at least 1.3 atm. In one embodiment, the pressure differential may be at least 2 atm. In one embodiment, the pressure differential may be at least 2.6 atm. In one embodiment, the pressure differential may be between 1.2 atm and about 3 atm. In one embodiment, the pressure differential may be between about 2 atm and about 3 atm. In one embodiment, the pressure differential may be between about 2.2 atm and about 2.6 atm. It is believed that the burst pressure differential accounts for an increase in stress in the remaining balloon (i.e., outer balloon 16B) when the other balloon (i.e., inner balloon 16A) bursts as the same pressure applied to both the balloons is then applied to just the remaining balloon. The increase in stress in the remaining (outer) balloon causes that balloon to expand. The expansion of the remaining balloon in turn reduces the pressure in the balloon. Because the remaining balloon is stronger than the burst balloon by a threshold amount, the remaining balloon can expand enough to allow the pressure in the balloon to drop below the burst pressure of the remaining balloon. Therefore, the remaining balloon will not burst. Thus, by providing the increased difference in target burst pressures, the stronger balloon is able to remain intact after the weaker balloon bursts. Conventional nested balloon assemblies fail to appreciate this phenomenon and thus do not select the appropriate relative burst pressures for the balloons when constructing the balloon assemblies.

A correlation between a balloon thickness of the balloons in a nested balloon assembly and the burst pressure of the balloons has been identified. Therefore, a thickness of each balloon in a nested balloon assembly may be selected to produce a target burst pressure for each balloon that maintains the overall burst pressure of the balloon assembly and provides the desired burst pressure differential between the balloons. Table I below shows examples of balloon thicknesses and the resulting burst pressures for an inner and outer balloon that achieve a desired relative burst pressure (Delta P) between the balloons. It can further be seen from Table I that the total thickness of the nested balloon assembly is kept constant while the relative thicknesses of the individual balloons are adjusted to achieved the desired burst pressure differentials. It will be understood that other characteristics of the balloons may be modified to achieve the desired relative burst pressures of the balloons in the nested balloon assembly. Further, while specific balloon thicknesses are provided, these are examples and it is contemplated that other thicknesses for the inner and outer balloons may be used to achieve the desired effects described herein.

TABLE I

Balloon Thickness - Burst Pressure Correlation

| Total Thickness of Balloon Assembly (mm) | Inner Balloon Thickness (mm) | Inner Burst Pressure (atm) | Outer Balloon Thickness (mm) | Outer Burst Pressure (atm) | Burst Pressure Differential (atm) | Overall Burst Pressure (atm) |
| --- | --- | --- | --- | --- | --- | --- |
| 0.15 | 0.075 | 12.09 | 0.0846 | 13.29 | 1.2 | 24.2 |
| 0.15 | 0.065 | 12.04 | 0.0854 | 13.24 | 1.3 | 24.1 |
| 0.15 | 0.057 | 11.59 | 0.0926 | 13.79 | 2.2 | 23.2 |
| 0.15 | 0.054 | 11.39 | 0.0958 | 13.9 | 2.6 | 22.8 |

It will be understood that a balloon burst occurs when the inflation pressure within the balloon reaches or exceeds the burst pressure of the balloon. The intended construction of a balloon will be such that the inflation pressure is less than the burst pressure so that a balloon burst does not occur. However, as will also be understood, the manufacturing process of an article will lead to variations in the properties of that article. Thus, a standard deviation will exist for any given characteristic of the article. This is the case for inflation and burst pressures for a given balloon. Therefore, despite the intended construction, there can exist an instance where a balloon's actual inflation pressure will equal or exceed the actual burst pressure of the balloon. More often than not, however, a balloon burst occurs when a clinician inflates the balloon beyond the stated burst pressure.

It is has been found that selecting the burst pressure differential between the balloons 16A, 16B, and knowing the pressure range within which both balloons will burst based on the selected burst pressures, can be used to predict the occurrence and type of balloon burst (e.g., inner only, outer only, and inner and outer balloons) that will occur. This allows for the enhancement of the overall safety profile of the balloon assembly 12.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

In one example, a burst rate prediction model is used to determine the likelihood of a particular mode of balloon burst. To make this prediction, a few factors may be assumed. First, the overall burst rate of a balloon can be estimated based on the comparison of clinical study data characterizing the mean inflation pressure and mean burst pressure of a standard medical balloon taking into account their standard deviations. In one example, this rate is estimated to be 0.5%. Next, the difference in burst pressure sufficient to leave one balloon intact when the other balloon bursts is assumed to be 0.75 atm, based on testing of nested balloon assemblies. The standard deviation of burst strength is assumed to be 1.0 atm, based on testing of the balloon layers separately. Below is a table of the data used in the burst prediction model to produce the target safety profile.

TABLE I

| Input Data for Desired Safety Profile | |
| --- | --- |
| Outer-Inner Strength | 2.6 atm |
| Outer-Inner Standard Deviation | 1.414 atm |
| Window of 2-Ballon Burst | 0.75 atm |
| Overall Burst Rate | 0.5% |

Using the balloon burst prediction model of the current disclosure, the above data produced the burst rate profile below.

TABLE 2

| Burst Rate Profile | |
| --- | --- |
| Inner-Only Burst Rate | 0.4% |
| Outer-Only Burst Rate | 0.004% |
| 2-Balloon Burst Rate | 0.04% |

Accordingly, a target burst pressure differential of 2.6 atm and a 2-ballon burst window of 0.75 atm is proven to provide the desired less than 1 in 2,000 likelihood of having a burst that is not contained by an intact outer balloon. It will be understood that changing the values of the data inputs will alter the burst rates as well as the other parameters of the balloon data needed to achieve a desired likelihood of an uncontained burst. For example, reducing the 2-ballon burst window to 0.5 atm will reduce the predicted likelihood of an uncontained burst to less than 1 in 2,900. Alternatively, to maintain the 1 in 2,000 likelihood of an uncontained burst with the 2-balloon burst window of 0.5 atm, a target burst pressure differential of only 2.32 atm is needed.

Alternatively, reducing the balloon component burst standard deviation from 1.0 atm to 0.8 atm results in a nested balloon standard deviation of 1.13 reduced from 1.414. This change would produce a predicted likelihood of an uncontained burst of less than 1 in 3,900. Moreover, maintaining the 1 in 2,000 likelihood of an uncontained burst target at the reduced nested balloon standard deviation of 1.13 would result in needing a target burst pressure differential of only 2.2 atm.

These target burst pressure differential values sufficiently accommodate the increase in stress within the balloon assembly 12 when a balloon (e.g., inner balloon 16A) bursts so that another balloon in the assembly (e.g., outer balloon 16B) does not also burst. The target burst pressure differential values also account for the standard deviation in the inflation pressures and bust pressures of the individual balloons 16A, 16B so that the actual burst pressures of the balloons maintain a sufficient burst pressure differential for ensuring that the balloon assembly 12 functions as intended. Further, focusing on the target burst pressure differential by reducing the strength of the inner balloon 16A rather than increasing the strength of the inner balloon allows for the overall burst pressure of the balloon assembly 12 to be substantially maintained. Therefore, the burst prediction model of the present disclosure provides a means for appropriately selecting the relative target burst pressures of the balloons to achieve the desired likelihood of an uncontained burst within the parameters of the balloon specifications.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A medical balloon assembly comprising an inner balloon nested within an outer balloon, the inner balloon having a first target burst pressure at which the inner balloon bursts and the outer balloon having a second target burst pressure at which the outer balloon bursts, a differential between the first and second target burst pressures being sufficient to allow the outer balloon to remain intact upon inflation of the inner and outer balloons causing the inner balloon to burst, wherein the inner balloon is formed separately from the outer balloon and each of the inner and outer balloons comprise a single piece of monolithic material, the inner and outer balloons being mounted on a catheter, ends of the inner and outer balloons being mounted on the catheter at a same location,
   wherein the first target burst pressure is based on an average burst pressure of 10 balloons having the same construction as the inner balloon,
   wherein the second target burst pressure is based on an average burst pressure of 10 balloons having the same construction as the outer balloon,
   wherein the first target burst pressure is lower than the second target burst pressure,
   wherein the differential between the first and second target burst pressures is above 1.2 atm and no greater than about 3 atm.

2. A medical balloon assembly as set forth in claim 1, wherein the differential between the first and second target burst pressures is at least 2.6 atm.

3. A medical balloon assembly as set forth in claim 1, wherein the inner and outer balloons have a combined thickness of greater than 0.1 mm and less than about 0.2 mm.

4. A medical balloon assembly as set forth in claim 3, wherein the inner and outer balloons have a difference in thickness ranging between about 0.019 mm and about 0.042 mm.

5. A medical balloon assembly as set forth in claim 1, wherein the differential between the first and second target burst pressures is at least 1.3 atm.

6. A medical balloon assembly as set forth in claim 5, wherein the differential between the first and second target burst pressures is at least 2 atm.

7. A medical balloon assembly as set forth in claim 1, wherein the inner and outer balloons are compliant.

8. A medical balloon assembly as set forth in claim 1, wherein each of the first target burst pressure and the second target burst pressure is greater than 10 atm.

9. A medical balloon assembly as set forth in claim 8, wherein the inner balloon has a thickness less than a thickness of the outer balloon.

10. A medical balloon assembly as set forth in claim 9, wherein the inner and outer balloons have a combined thickness of greater than 0.1 mm and less than about 0.2 mm.

11. A medical balloon assembly as set forth in claim 10, wherein the inner and outer balloons have a difference in thickness ranging between about 0.019 mm and about 0.042 mm.

12. A medical balloon assembly as set forth in claim 1, wherein an inflatable portion of the inner balloon is configured to expand an entirety of an expandable portion of the outer balloon as the inner balloon is inflated.

13. A medical balloon assembly as set forth in claim 1, wherein a likelihood that the outer balloon does not remain intact if the inner balloon bursts is less than 1 in 2,000.

14. A method of making a medical balloon assembly, the method comprising:
   forming a first balloon from a single piece of monolithic material having a first target burst pressure at which the first balloon bursts, wherein the first target burst pressure is based on an average burst pressure of 10 balloons having the same construction as the inner balloon;
   forming, separately from the first balloon, a second balloon from a single piece of monolithic material having a second target burst pressure at which the second balloon bursts, wherein the second burst pressure is based on an average burst pressure of 10 balloons having the same construction as the outer balloon, wherein the first target burst pressure is lower than the second target burst pressure, wherein a differential between the first and second target burst pressures is above 1.2 atm and no greater than about 3 atm;
   nesting the first balloon in the second balloon, the differential between the first and second target burst pressures being sufficient to allow the second balloon to remain intact upon inflation of the first and second balloons causing the first balloon to burst; and
   mounting the first and second balloons to a catheter such that ends of the first and second balloons are mounted on the catheter at a same location.

15. A method as set forth claim 14, further comprising adjusting a thickness of each of the first and second balloons to achieve the differential between the first and second target burst pressures.

16. A method as set forth in claim 15, further comprising forming the first and second balloons to have a combined thickness of less than about 0.2 mm.

17. A method as set forth in claim 16, further comprising forming the first and second balloons to have a difference in thickness ranging between about 0.019 mm and about 0.042 mm.

18. A method as set forth in claim 14, wherein a likelihood that the outer balloon does not remain intact if the inner balloon bursts is less than 1 in 2,000.

19. A medical balloon assembly comprising an inner balloon nested within an outer balloon, the inner balloon having a first target burst pressure at which the inner balloon bursts and the outer balloon having a second target burst pressure at which the outer balloon bursts, a differential between the first and second target burst pressures being sufficient to allow the outer balloon to remain intact upon inflation of the inner and outer balloons causing the inner balloon to burst, wherein the inner balloon is formed separately from the outer balloon and each of the inner and outer balloons comprise a single piece of monolithic material, the inner and outer balloons being mounted on a catheter, ends of the inner and outer balloons being mounted on the catheter at a same location, wherein the first target burst pressure is based on an average burst pressure of 10 balloons having the same construction as the inner balloon, wherein the second burst pressure is based on an average burst pressure of 10 balloons having the same construction as the outer balloon, wherein the first target burst pressure is lower than the second target burst pressure, wherein the differential between the first and second target burst pressures is above 1.2 atm and no greater than about 3 atm, wherein an inflatable portion of the inner balloon extends along an entirety of an expandable portion of the outer balloon such that the inner balloon is configured to expand an entirety of an expandable portion of the outer balloon as the inner balloon is inflated.

20. A medical balloon assembly as set forth in claim 19, wherein a likelihood that the outer balloon does not remain intact if the inner balloon bursts is less than 1 in 2,000.

* * * * *